(12) United States Patent
Lett et al.

(10) Patent No.: US 11,713,284 B1
(45) Date of Patent: Aug. 1, 2023

(54) METHODS OF PRODUCING FERTILIZER COMPOSITIONS AND BIOGAS

(71) Applicant: Farment Bio Solutions Ltd., Vernon (CA)

(72) Inventors: Ralph Jeffery Lett, Vernon (CA); Jorge Ignacio Martinez Casas, Kelowna (CA); Facundo Martin Rapela, Vernon (CA)

(73) Assignee: Farment Bio Solutions Ltd., Vernon (CA)

( * ) Notice: Subject to any disclaimer, the term of this patent is extended or adjusted under 35 U.S.C. 154(b) by 0 days.

(21) Appl. No.: 18/087,183

(22) Filed: Dec. 22, 2022

(51) Int. Cl.
| | | |
|---|---|---|
| C05G 1/00 | (2006.01) | |
| C05F 17/10 | (2020.01) | |
| C12P 5/02 | (2006.01) | |
| C05F 11/02 | (2006.01) | |
| C05C 1/00 | (2006.01) | |
| C05F 3/00 | (2006.01) | |

(52) U.S. Cl.
CPC ............. *C05G 1/00* (2013.01); *C05C 1/00* (2013.01); *C05F 3/00* (2013.01); *C05F 11/02* (2013.01); *C05F 17/10* (2020.01); *C12P 5/023* (2013.01)

(58) Field of Classification Search
None
See application file for complete search history.

(56) References Cited

U.S. PATENT DOCUMENTS

| | | | | |
|---|---|---|---|---|
| 2012/0024781 A1* | 2/2012 | Lugo | ..................... | C02F 11/04 210/601 |
| 2014/0144195 A1* | 5/2014 | Callendrello | ............. | C05C 9/00 60/39.12 |
| 2015/0329399 A1* | 11/2015 | Kumar | .................... | C05F 17/15 71/10 |

(Continued)

FOREIGN PATENT DOCUMENTS

| | | | | | |
|---|---|---|---|---|---|
| CA | 2727662 | * | 12/2009 | ............. | C05F 17/02 |
| CN | 110760547 A | * | 2/2020 | ............... | C05F 3/00 |
| CN | 112586130 A | * | 4/2021 | ............. | C05F 11/00 |

(Continued)

OTHER PUBLICATIONS

Takasaki, K. et al., "Fungal Ammonia Fermentation, a Novel Metabolic Mechanism That Couples the Dissimilatory and Assimilatory Pathways of Both Nitrate and Ethanol", Dec. 16, 2003. DOI 10.1074/jbc.M313761200, ISSN-2314-3126.

(Continued)

*Primary Examiner* — Wayne A Langel
(74) *Attorney, Agent, or Firm* — Oyen Wiggs Green & Mutala LLP

(57) ABSTRACT

A method of producing fertilizer compositions while producing biogas is disclosed. The method comprises converting an organic material such as organic wastes into fertilizer compositions and biogas. The conversion of the organic material is performed in a fermentation process. In some embodiments, the method comprises preparing a fermenting mixture comprising a starting organic material, a starting bio-stimulant product comprising a plurality of microorgan- (Continued)

isms, and a starting nitrogen source, and fermenting the fermenting mixture in a fermentation environment for a first time interval to form a fermented mixture comprising the fertilizer composition.

15 Claims, 2 Drawing Sheets

(56) References Cited

U.S. PATENT DOCUMENTS

| 2022/0144717 A1* | 5/2022 | Lett | C12N 1/14 |
| 2023/0022971 A1* | 1/2023 | Burnham | C05F 9/00 |

FOREIGN PATENT DOCUMENTS

| CN | 113979794 A | * | 1/2022 | C05F 17/20 |
| DE | 102015010041 | * | 2/2017 | C05F 11/02 |
| IN | 201727006427 A | * | 5/2017 | C12P 7/40 |
| KR | 20150048991 A | * | 5/2015 | C02F 3/28 |
| WO | 2013186608 A1 | | 12/2013 | |

OTHER PUBLICATIONS

Zhou, Z., Takaya, N., Nakamura, A., Yamaguchi, M., Takeo, K., and Shoun, H., Ammonia fermentation, a novel anoxic metabolism of nitrate by fungi. J. Biol. Chem., 277, 1892-1896 (2002).

* cited by examiner

METHODS OF PRODUCING FERTILIZER COMPOSITIONS AND BIOGAS

FIELD OF THE INVENTION

The invention pertains to generally to methods of producing fertilizer compositions and biogas, more particularly, methods of producing fertilizer compositions while producing biogas from organic materials such as organic wastes.

BACKGROUND OF THE INVENTION

Methods of producing fertilizer compositions are known in the art. The present invention is directed to improved methods of producing fertilizer compositions which contain sources of nitrogen that are available for uptake by plants, while producing useful byproducts such as biogas.

SUMMARY

Aspects of the invention pertain to methods of producing fertilizer compositions while producing biogas. In some embodiments, the methods comprise converting organic materials such as organic wastes into useful products. Such useful products include fertilizer compositions and biogas. The produced biogas may for example be useful for heating and power generation. The conversion of organic materials comprises a fermentation process. In some embodiments, the fermentation process increases the total nitrogen concentration in the input materials so as to produce fertilizer compositions comprising sources of nitrogen that are available for uptake by plants.

In some embodiments, the method comprises preparing a fertilizing mixture by combining a starting organic material, a starting bio-stimulant product comprising a plurality of microorganisms, and a starting nitrogen source. The fertilizing mixture is subjected to a fermentation step in a fermentation environment for a first time interval to form a fermented mixture comprising the fertilizer composition. In some embodiments, the total concentration of nitrogen in the fermented mixture is greater than a total combined concentration of nitrogen in the starting organic material and the starting nitrogen source. In some embodiments, the total concentration of nitrogen in the fermented mixture is about 1.5 to about 2 times greater than the total combined concentration of the nitrogen in the starting organic material and the starting nitrogen source.

In some embodiments, biogas produced from the fermenting of the fertilizing mixture is collected during or after the time interval.

In some embodiments, the starting organic material is an organic waste. The organic waste may for example be one or more of an animal waste such as manure, agricultural waste such as humus, crop wastes, and digestate.

In some embodiments, the starting nitrogen source comprises an inorganic source of nitrogen and/or an organic source of nitrogen. The starting nitrogen source may comprise any one or more of a salt, free amino acids, peptides, and/or proteins. In some embodiments, the starting nitrogen source is derived from atmospheric air. In some embodiments, the starting nitrogen source comprises nitrogenous waste such as blood and/or urine.

In some embodiments, the fermentation environment comprises an acidic pH in the range of from about 3.5 to about 5.5. In some embodiments, the fermentation environment comprises oxygen-limited conditions. In some embodiments, the fermentation environment comprises a temperature in the range of from about 20° C. to about 35° C. In some embodiments, the first time interval is in the range of from about 5 to about 10 days.

In some embodiments, the method comprises adding water to the fertilizing mixture before the step of fermenting the fertilizing mixture. The water may first be prepared by reducing a pH of the water.

In some embodiments, a carbon nanomaterial is added to the prepared water before the step of fermenting the fertilizing mixture.

The fermented mixture is collected after the fermentation step. In some embodiments, a liquid fraction and a solid fraction are separated from the fermented mixture. The liquid fraction may be reused in subsequent fermentation processes. In some embodiments, the liquid fraction is added to the fertilizing mixture before the fermentation step.

In some embodiments, the starting bio-stimulant product is produced from a plant material. The plant material may for example be humus. The starting bio-stimulant product comprises a plurality of microorganisms. The plurality of microorganisms may comprise facultative anaerobic organisms.

In some embodiments, the starting bio-stimulant product is prepared by the steps of preparing a first mixture comprising a starting material, a first carbohydrate and water, placing the first mixture in a microorganism growth environment for a second time interval so as to cultivate the at least one microorganism, preparing a second mixture by adding a second carbohydrate to the first mixture, and fermenting the second mixture in a second fermentation environment for a third time interval so as to produce the starting bio-stimulant product.

In some embodiments, one or more fertilizer ingredients are added to the first mixture in the preparation of the second mixture, before the step of fermenting of the second mixture.

Further aspects of the invention and features of specific embodiments of the invention are described below.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Figure 1:
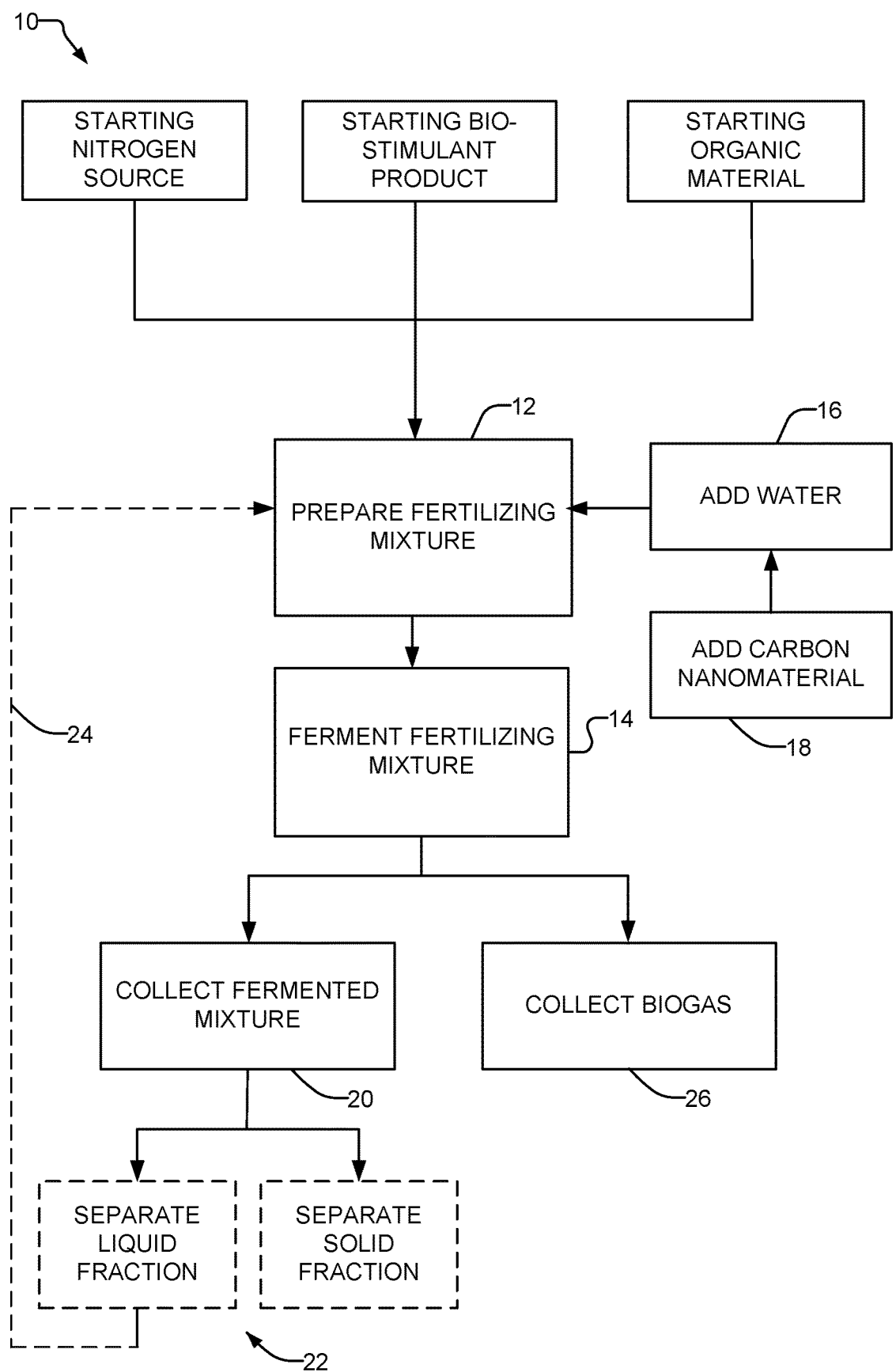
FIG. 1 illustrates a method of preparing a fertilizer composition according to example embodiments of the invention.

One aspect of the invention pertains to methods of producing fertilizer compositions. Referring to FIG. 1, the method 10 comprises preparing a fertilizing mixture by combining a starting organic material, a starting bio-stimulant product, and a starting nitrogen source (step 12).

The starting organic material may be an organic waste. The organic waste may for example be animal waste such as manure and fodder, agricultural waste (e.g., crop waste, maize silage), food waste, plant waste, etc. In some embodiments, the organic waste is digestate, i.e., the substance produced by anaerobic digestion. Other organic materials such as other biomass, living organisms such as a plant (e.g., algae and herbs such as mint, oregano) may be used. The organic waste may be generated by a single source or a plurality of sources.

In some embodiments, the starting organic material is treated prior to combining with the starting nitrogen source and the starting bio-stimulant product. The starting organic material may for example be physically treated by shredding or grinding of the material to reduce the size of the material. In other example embodiments, the starting organic material is treated by separating (e.g., by any suitable solid-liquid separation means such as gravity or mechanical systems) the liquid materials from the solid materials. In other example embodiments, the starting organic material is chemically treated.

The starting nitrogen source may be a natural nitrogen source and/or a synthetic nitrogen source. The starting nitrogen source may be an inorganic nitrogen source, an organic nitrogen source, or a combination thereof. The starting nitrogen source may be in a gaseous form and/or a liquid form. The organic nitrogen source may in some embodiments comprise one or more of free amino acids, proteins and peptides including for example, tripeptides. The inorganic nitrogen source may in some embodiments comprise one or more compounds containing nitrate ($NO_3^-$) ions, compounds containing nitrite ($NO_2^-$) ions, ammonia ($NH_3$), dinitrogen or nitrogen gas ($N_2$) and derivatives thereof. Non-limiting example of a inorganic nitrogen source is a salt such as ammonium sulphate or ammonium nitrate.

In some embodiments, the starting nitrogen source is generated from atmospheric air. In some embodiments, the starting nitrogen source is generated by separating nitrogen gas ($N_2$) from atmospheric air using a nitrogen extractor. Different methods of separating nitrogen gas from atmospheric air may be applied, for example, by methods such as cryogenic distillation, pressure swing adsorption, and membrane nitrogen generation. In some embodiments, the separated nitrogen gas is converted to the starting nitrogen source. The separated nitrogen gas may chemically react with one or more oxygen gas and hydrogen gas to form the starting nitrogen source. In some embodiments, the chemical reaction is performed in the presence of a catalyst, such as for example, a metal catalyst e.g., iron, molybdenum, vanadium, palladium, copper and the like.

In some embodiments, the starting nitrogen source comprises nitrogenous wastes. "Nitrogenous wastes" are waste products generated as the end products of protein metabolism. Non-limiting examples of nitrogenous waste include blood and/or urine.

In some embodiments, the starting nitrogen source comprises a single source of nitrogen. In some embodiments, the starting nitrogen source comprises a mixture of two or more different sources of nitrogen.

The starting bio-stimulant product comprises a plurality of microorganisms. The plurality of microorganisms may comprise one or more types of facultative anaerobic microorganisms. Facultative anaerobic microorganisms are microorganisms which do not require oxygen in the environment to survive. In some embodiments, the plurality of microorganisms are substantially or in some embodiments essentially facultative anaerobic microorganisms. Facultative anaerobic microorganisms may be certain types of bacteria or fungi. Non-limiting examples of facultative anaerobic organisms include *Staphylococcus* spp., *Escherichia coli, Salmonella, Listeria* spp., *Shewanella oneidensis, Yersinia pestis, Saccharomyces cerevisiae*, and *Fusarium oxysporum*. In some embodiments, the plurality of microorganisms comprise at least one strain of fungus. In some embodiments, the starting bio-stimulant product is produced from a starting material obtained from a natural environment. In some example embodiments, the starting material comprises one or more of humus, soil, and foliage.

In some embodiments, the fertilizing mixture comprises more than 50% wt. of the organic materials, or in some embodiments, more than 60% wt., or in some embodiments, more than 70% wt., or in some embodiments, in the range of from about 50% to about 90% wt., or in some embodiments in the range of from about 60% to about 85% wt., or in some embodiments, in the range of from about 70% to about 80% wt.

In some embodiments, the fertilizing mixture comprises about 2% to 20% wt. of the starting bio-stimulant product, or in some embodiments, about 5% to 15% wt., or in some embodiments, about 6% to about 12% wt.

In some embodiments, the fertilizing mixture comprises about 0.2% to 5% wt. of the starting nitrogen source, or in some embodiments, about 0.5% to about 3% wt., or in some embodiments about 0.8% to about 2% wt.

In some embodiments, the fertilizing mixture is subjected to a fermentation step (step 14). The fertilizing mixture may be fermented in a fermentation environment for a first time interval.

In some embodiments, the fermentation environment comprises low oxygen conditions or oxygen-limited conditions. In such embodiments, oxygen is not supplied to the fermentation process. The inventors believe that supplying oxygen to the fermentation process or exposing the microorganisms in the starting bio-stimulant product to excess oxygen may in some embodiments undesirably promote the growth of pathogens such as *Escherichia coli* (*E. coli*) and the like. In some example embodiments, the fermentation is performed in a sealed bioreactor. The sealed bioreactor may for example be an airtight bag.

In some embodiments, the fermentation environment comprises maintaining a temperature in the range of from about −20° C. to about 40° C., or from about 20° C. to about 35° C. In some embodiments, the temperature maintained in the fermentation environment is about 30° C.

In some embodiments, the fermentation environment comprises an acidic environment. In some embodiments, the fermentation environment comprises a pH in the range of from about 2.2 to about 6, or in some embodiments, between about 3.5 to about 5.5.

In some embodiments, the first time interval is in the range of from about four to about 14 days, or about five to about 10 days, or about seven days. The first time interval may be adjusted based on the temperature maintained in the fermentation environment. For example, the fertilizing mixture may be subjected to fermentation for a longer time period when the fermentation is performed in a low temperature, and be subjected for a shorter time period when the fermentation is performed in a high temperature.

In some embodiments, the method 10 comprises adding water to the bioreactor (step 16). The water may be added to the bioreactor before the addition of the fertilizing mixture or the components thereof (i.e., starting organic material, starting bio-stimulant product, and starting nitrogen source). In some embodiments, the water is added directly to the fertilizing mixture. In some embodiments, the amount of water to add to the bioreactor depends on the moisture content of the fertilizing mixture. In some embodiments, a sufficient amount of water is added to the fertilizing mixture to achieve a moisture content of the fertilizing mixture of about 60% to 95%. In some embodiments, water is not added to the bioreactor. In such embodiments, the fertilizing mixture (before the addition of water) has a moisture content of about 60% to 95% so no added water is required. In some embodiments, the fertilizing mixture preferably has the texture and/or appearance of wet mud.

In some embodiments, the water is prepared to create an environment that is favourable for fermentation. The water may be prepared prior to or after the adding of the water to the bioreactor. An environment that is favourable for fermentation may include reducing the pH within the bioreactor to an acidic environment, such as a pH of about 2.0 to 8.5, or preferably between 2.5 to 5.5. In example embodiments, the water is prepared by adding dry ice (i.e., a solid form of carbon dioxide $CO_2$) to the water within the bioreactor. The dry ice dissolves in water to create carbonic acid ($H_2CO_3$), thereby reducing the pH within the bioreactor. In one example embodiment, 10 pounds (lbs) of dry ice per thousand liters (L) of water is added to the bioreactor.

In some embodiments of the method, a carbon nanomaterial is added to the prepared water (step 18), before or after preparing the mixture and/or adding of the one or more fertilizer ingredients. The carbon nanomaterial may be in the form of one or more of carbon nanotubes (CNT), which includes single-walled carbon nanotubes (SWCNTs) and double-walled carbon nanotubes (SWCNTs), graphene, fullerenes ($C_{60}$), carbon nanoonions (CNOs), nanorods, graphene quantum dots (GQDs), photoluminescent carbon dots (CDs) and the like. In an example embodiment, the carbon nanomaterial is a carbon nanotube.

The carbon nanomaterial may be treated before adding to the prepared water. In some embodiments, the carbon nanomaterial is treated by sonication or other suitable means to promote the dispersion of the nanomaterials. The carbon nanomaterial may be dispersed in a dispersion liquid. The dispersion liquid may for example include a solvent (e.g, water or an organic solvent such as alcohol) and/or surfactant. In some embodiments, the surfactant is a polymeric surfactant. In an example embodiment, the surfactant is a cellulose-based polymeric surfactant. Other suitable surfactants such as cetyltrimethylammonium bromide, Triton X-100, sodium dodecylbenzene sulfonate (SDBS) may also be used. The surfactant may be added to the carbon nanomaterial in the treatment step (i.e., as a dispersion liquid), or after the treatment step. For example, the surfactant may be added to the dispersed carbon nanomaterial after the sonication step before or after the dispersed carbon nanomaterial has been added to the bioreactor.

In example embodiments, the concentration of carbon nanomaterials is about 0.01 wt % to about 0.2 wt %, and in some embodiments between about 0.02 wt % and about 0.08 wt %.

The fermented mixture is collected after the fermentation step (step 20). The collected fermented mixture may be filtered to separate the solid and liquid fractions (step 22).

In some embodiments, the liquid fraction is recycled for use in subsequent fermentation processes (step 24). In some embodiments, in a subsequent fermentation process, the separated liquid fraction is added to the fertilizing mixture before the fermentation step. In some embodiments, the liquid fraction is added to the fertilizing mixture in addition to the water. In other embodiments, the liquid fraction is added in place of the water. The inventors consider that the addition of the liquid fraction of the fermented mixture increases the speed of the fermentation process.

In some embodiments, the fermented mixture is further processed by granulation or pelletized by any suitable methods to form fertilizer particles. Alternatively, the fermented mixture which serves as the fertilizer product is applied directly to crops.

The inventors consider that fermenting the starting organic material with the starting bio-stimulant product and the starting nitrogen source promotes an increase in the total combined nitrogen concentration in the starting organic material and the starting nitrogen source. In some embodiments, the total nitrogen concentration contained in the fermented mixture is greater than the combined total nitrogen concentration contained in the starting organic material and the starting nitrogen source. In some embodiments, the total nitrogen concentration contained in the fermented mixture is at least about 1.5 times greater than the combined total nitrogen concentration contained in the starting organic material and the starting nitrogen source. In some embodiments, the total nitrogen concentration contained in the fermented mixture is about 1.5 to about 2 times greater than the combined total nitrogen concentration contained in the starting organic material and the starting nitrogen source.

In some embodiments, the nitrogen source in the fermented mixture comprises one or more elements (including ions, molecules, atoms, and/or compounds) which are in a form of nitrogen that is available for uptake by plants. The nitrogen source may for example comprise ammonium ($NH_4^+$), or a derivative thereof, or in the form of one or more of proteins, peptides (including for example tripeptides), and free amino acids. Non-limiting examples of free amino acids that may be found in the fermented mixture include alanine, asparagine, aspartate, glutamate, glutamine, histidine, lysine, arginine, proline, and tryptophan.

In some embodiments, biogas is produced in the fermentation of the fertilizing mixture. The biogas may comprise a mixture of gases. The mixture of gases may include methane ($CH_4$), carbon dioxide ($CO_2$) and other gases such as hydrogen sulphide ($H_2S$). Some embodiments of the invention involve collecting the biogas (step 26) produced from the fermentation step. The produced biogas may be collected at the end of the fermentation step, or collected throughout the fermentation step at timed intervals. For example, the produced biogas may be collected once every three hours throughout the fermentation step.

The collected biogas may be purified to separate methane from carbon dioxide and/or other gases. Any suitable methods conventionally used to purify biogas may be applied, for example, water scrubbing, adsorption (physical and chemical), cryogenic separation, membrane separation, biological upgrading and in-situ upgrading methods.

In some embodiments, about 8 $m^3$/25 h to about 15 $m^3$/24 h of biogas is produced from fermenting about 300 to 400 kg/day of starting organic material using the methods of the embodiments of the present invention, or in some embodiments, in the range of from about 9 $m^3$/24 h to about 13 $m^3$/24 h.

In some embodiments, the fermented mixture comprises about 20 to 40% of gaseous compounds (e.g., one or more of methane, carbon dioxide, hydrogen sulphide, etc.), about 50% to about 80% of liquid, and about 20% to 40% of solid.

The Starting Bio-stimulant Product and Methods of Making Same

Figure 2:
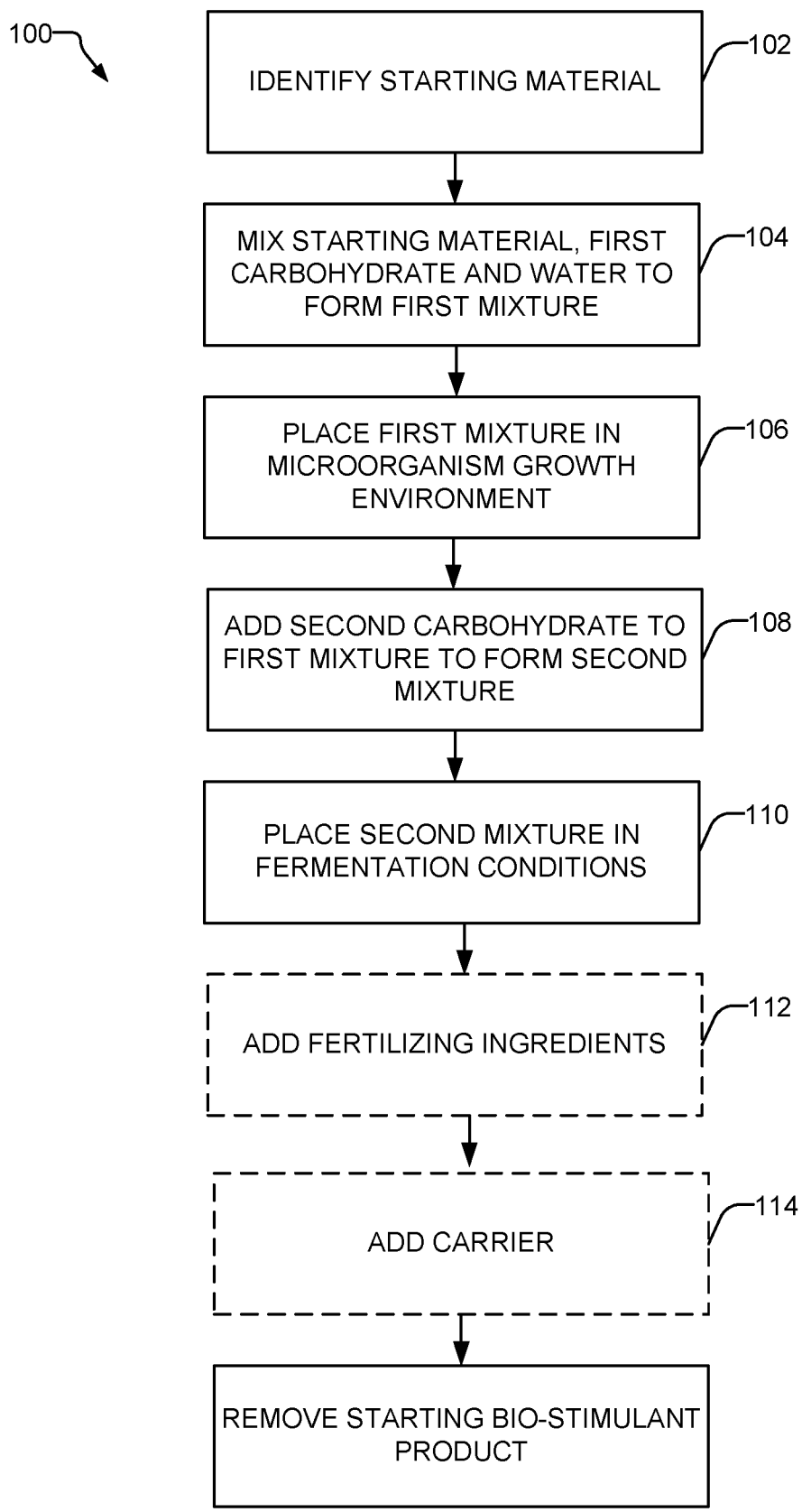
FIG. 2 illustrates a method of preparing a starting bio-stimulant product for use in the FIG. 1 method of preparing the fertilizer composition according to example embodiments of the invention.

Aspects of the invention pertain to producing a bio-stimulant product suitable for use as the starting bio-stimulant product in the methods of producing the fertilizer composition 10. Referring to FIG. 2, in some embodiments, the method 100 begins with identifying an appropriate starting material (step 102). The starting material may be a microbial sample obtained from a natural environment. A natural environment comprises microorganisms that exist in their natural ecosystems and excludes the presence of laboratory microorganisms. Laboratory microorganisms are microorganisms that are grown under laboratory conditions. Such conditions are typically optimized to favour the growth of certain microorganisms. Different plants are adapted to grow in different soil compositions, and growing them in the wrong type of soil can be harmful to their health and growth. Healthy soil is the basis for a healthy and strong plant. Thus, the starting material may be chosen based on the plant intended to be grown. For example, if the targeted plant is a blueberry bush, the starting material may be taken from the soil of a blueberry bush that is a healthy, high yielding plant. The soil from a healthy blueberry bush will contain the diverse plurality of a group of microorganisms and nutrients necessary to enhance the growth of subsequent blueberry plants.

A further example of an appropriate starting material may comprise compost or humus, which contains the desired level of living biological activity. Compost or humus may contain microorganisms such as, *lactobacillus*, phosphate solubilizing bacteria, photosynthesizing bacteria and fermenting fungi and yeast. The compost or humus may contain one type of organic materials or a blend of different types or species of organic materials. Examples of suitable organic materials include for example plant materials such as leaves and grass, food waste such as fruit and vegetable peels, wood chips, or any other suitable compostable materials. In one example embodiment, the starting material is a decomposed leaf litter. Additionally, such starting materials may also include different mixtures of certain micronutrients which are desirable for promoting healthy plant growth.

Without intending to be limiting, the inventors have sourced fungal dominated forest humus which has tremendous beneficial microbial diversity, and also includes various different micronutrients including in particular calcium, magnesium, copper, zinc, manganese and iron in quantities which are optimal for promoting healthy plant growth. The term "fungal dominated" as used herein means greater colony forming units of fungi than bacteria. The fungi found in fungal dominated forest humus aid in suppressing pathogenic organisms and in creating healthy soil biology. In addition, the fungal dominated forest humus starting material includes smaller quantities of available nitrogen, phosphorus, potassium, and boron which again support the healthy growth of plants. Importantly, the forest humus source identified by the applicant for producing the starting bio-stimulant product does not contain harmful bacteria or plant disease pathogens, according to analyses conducted on the starting material.

Other appropriate starting materials may contain different mixtures of microorganisms and micronutrients, or may not have any micronutrients or negligible amounts of micronutrients. Other examples of compounds or substances in a starting material that may be useful include fluvic and humic acid, which may increase the absorption of the microorganisms by the carrier.

Once an appropriate starting material has been identified, the process for producing a starting bio-stimulant product may include preparing a first mixture comprising the identified starting material, a first carbohydrate, and water (step 104).

Carbohydrates are a fuel source for microorganisms and play an important role in the growth and multiplication of microorganisms. Adding carbohydrates to the starting material promotes the growth of the beneficial microorganisms. In some embodiments, the first carbohydrate is at least one starch. The prepared first mixture is placed into a microorganism growth environment for a given time interval so as to facilitate the growth and multiplication of the microorganisms which exist in the starting material. In some example embodiments, the ratio of components in the aqueous mixture would be approximately 80% starting material, 10% water and 10% carbohydrate by volume.

An appropriate carbohydrate may include, for example, oats, rice, any others type of carbohydrates such as barley, grains, potato meal, cornstarch, coconut husks, peat, woodchips, corn or any other appropriate carbohydrates for promoting the growth of the targeted microorganisms, such as bacteria and fungi. Another carbohydrate source may include brewery waste, otherwise referred to as spent grain or leftover beer mash. Optionally, the carbohydrates may be ground up so as to increase the surface area of the carbohydrates in the aqueous mixture for the beneficial microorganisms to feed upon. In other embodiments in which a remediation product is produced, the food source for a remediation product containing nitrate-reducing bacteria may include chicken manure or other appropriate materials containing nitrate for the nitrate-reducing bacteria to feed upon.

Once the first mixture is prepared, it may be placed in a microorganism growth environment which promotes the growth of the beneficial microorganisms that are desired to be produced (step 106). For example, the inventors have found that placing the first mixture in a dark environment in which there is no light or air, combined with maintaining a temperature in that environment of approximately 30° C. for a first time interval of approximately one week effectively enables the beneficial microorganisms to multiply to the required concentrations for producing the starting bio-stimulant. However, it will be appreciated by a person skilled in the art that other microorganism growth environments may be appropriate for promoting the growth of beneficial microorganisms. For example, the temperature may vary in the range between 5° C. and 40° C., depending on the particular types of microorganisms being grown. In other embodiments, for example, for producing remedial products containing bacteria, the temperature range may be between 15° C. and 40° C., depending on the type of bacteria being grown. In other example embodiments, the first mixture is maintained at low temperatures, such as at temperatures of below 5° C., or below 0° C., or below −10° C., or below −20° C. In some embodiments, the first mixture is maintained at a temperature between about −10° C. to about 30° C. The inventors have discovered that lower temperatures promote the growth of certain types of microorganisms such as certain types of fungi that may be desirable in certain applications. The microorganism growth environment need not be entirely anaerobic. In some embodiments, the microorganisms are placed in an environment which contains some oxygen.

The time interval for the microorganisms' growth need not be limited to seven days, and for example may be approximately in the range of four to fourteen days. The specific growing conditions for promoting microorganism growth may vary depending on the type of microorganisms which are being cultivated for the bio-stimulant or remediation product. The term "cultivate" as used herein means to grow. In the embodiments for producing a starting bio-stimulant containing a diverse group of microorganisms, for example, comprising *Torulaspora delbruekii, Acetobacter indonesiensis, Acetobacter orientalis, Acetobacter melorum*, and *Sporolactobacillus nakayamae*, or comprising *Lactobacillus mall, Paenibacillus glycanilyticus, Pichia membrani-*

*faciens, Pichia manshurica, Candida boidinii, Lachancea fermentati*, or comprising *Arthrobacter* sp., *Candida membranifaciens, Leuconostoc mesenteroides, Penicillium canescens, Geotrichum candidum*, or comprising *Torulaspora delbruekii, Bacillus subtilis, Leuconostoc mesenteroides, Brevibacterium frigoritolerans*, or comprising *Pichia membranifaciens, Wickerhamomyces anomalus, Weissella paramesenteroids, Bacillus megaterium, Leuconostoc mesenteroides, Raoultelle omithinolytica*, leaving the aqueous mixture in a lightless environment at a temperature of approximately 30° C. for approximately two to four weeks may result in sufficient microorganism growth.

Once the first mixture contains sufficient amounts of targeted beneficial microorganisms, a second carbohydrate, for example, at least one sugar, may be added to the first mixture to form a second mixture (step 108). The second mixture may then be placed into an environment adjusted for fermentation purposes for a time interval (step 110). For example, without intending to be limiting, sugar may be introduced to the second mixture at a ratio of one part sugar to two parts aqueous solution, by volume. The addition of sugar to the second mixture enables fermentation of the mixture. The inventors have found that this process produces a substantially homogenous, viscous mixture, without chunks of humus or other starting material. Any type of sugar may be used for the fermentation process and is intended to be included in the scope of the present disclosure. Without intending to be limiting, different types of sugars which may be added include cane sugar, beet sugar, molasses, or other appropriate types of sugar for encouraging fermentation. The fermentation promoting environment may include, for example, placing the second mixture with the sugar added into a dark environment in which there is no light or air (i.e., oxygen), and maintaining the temperature of the environment in the range of from about −10° C. to about 40° C., for embodiments to produce a starting bio-stimulant which contains a diverse group of microorganisms comprising, for example, *Torulaspora delbruekii, Acetobacter indonesiensis, Acetobacter orientalis, Acetobacter melorum*, and *Sporolactobacillus nakayamae*, or *Lactobacillus mall, Paenibacillus glycanilyticus, Pichia membranifaciens, Pichia manshurica, Candida boidinii, Lachancea fermentati*, or comprising *Arthrobacter* sp., *Candida membranifaciens, Leuconostoc mesenteroides, Penicillium canescens, Geotrichurn candidum*, or *Torulaspora delbruekii, Bacillus subtilis, Leuconostoc mesenteroides, Brevibacterium frigoritolerans*, or *Pichia membranifaciens, Wickerhamomyces anomalus, Weissella paramesenteroids, Bacillus megaterium, Leuconostoc mesenteroides, Raouftelle omithinolytica*. The time interval may for example be approximately one to two weeks. In other embodiments for producing remedial products containing bacteria, the environment may be maintained at a temperature in the range of 15° C. to 40° C. The fermentation process also results in the production of volatile fatty acids, enzymes, and metabolites, which all play a role in disease suppression and are used by microorganisms to assist with reproduction and growth. In addition to facilitating fermentation, the addition of sugar at this stage in the process may play a further role in extending the shelf life of the final starting bio-stimulant product, by providing a food source for the beneficial microorganisms. For example, without intending to be limiting, the shelf life of the final starting bio-stimulant product may be in the approximate range of one to two years. It will be appreciated by a person skilled in the art that the fermentation step described above, may be carried out more than once.

The fermentation step may be performed in the presence of at least some air (i.e., oxygen). In some embodiments, the fermentation step need not occur in a completely anaerobic environment. In some embodiments, additional water is not added to form the second mixture prior to the fermentation step, i.e., the fermentation step occurs after a second carbohydrate is added to the first mixture without the addition of water.

In some embodiments, the method is performed at a temperature in the range of from about −20° C. to about 40° C. In some embodiments, the method is performed at a temperature in the range of about 20° C. to about 35° C.

In some embodiments, one or more fertilizer ingredients are added to the first mixture and/or the second mixture (step 112) prior to the fermentation of the second mixture. The one or more fertilizer ingredients and the concentrations of each to add may be selected based on the blend of nutrients or the balance of nutrients (e.g., the specific ratio of nitrogen-phosphorus-potassium (NPK)) desired in the composition).

The one or more fertilizer ingredients may include one or more of macronutrient sources (i.e., elements that supply one or more of nitrogen (N), phosphorus (P), potassium (K), calcium (Ca), magnesium (Mg), and sulfur (S)), micronutrient sources (i.e., elements that supply one or more of boron (B), copper (Cu), iron (Fe), chloride (Cl), manganese (Mn), molybdenum (Mo) and zinc (Zn)), growth promoters, minerals, vitamins, amino acids, polysaccharides, or any other ingredients that may be useful to the treatment of crops such as for growth, survival, and/or repair. In some embodiments, the one or more fertilizer ingredients are sourced from one or more organic materials such as manure and agricultural waste, or other biomass, living organisms such as a plant (e.g., algae and herbs such as mint, oregano), minerals (e.g., zeolite), fermented products (e.g., alcohol and vinegar) and compounds including organic compounds such as organic acids (e.g., humic acid, fulvic acid, acetic acid, and citric acid), urea ($CO(NH_2)_2$), alcohol, and inorganic compounds such as inorganic acids (e.g., phosphoric acid) and metal salts (e.g., ammonium sulfate, ammonium phosphate, potassium nitrate, ammonium nitrate, potassium sulfate, potassium nitrate and calcium nitrate).

In some example embodiments, the one or more fertilizer ingredients comprise one or more of ammonium sulfate, seaweed, calcium carbonate, and acetic acid.

Once the fermentation is complete, the starting bio-stimulant is produced. In some embodiments, the fermentation is complete when the pH of the fermented mixture is below about 5, or below about 4.

Following fermentation, a carrier, such as water, zeolite, biochar, woodchips, or diatomaceous earth may be added to the starting bio-stimulant (step 114). It will be appreciated by a person skilled in the art that various types of material can be used as a carrier for the starting bio-stimulant product. Incorporation of beneficial microorganisms in a carrier enables easy handling and long term storage. Furthermore, the carrier can alter the pH of the soil. Soil pH can impact plant growth in several ways. Different microorganisms function best at different pH ranges. Soil pH may also impact the availability of micronutrients and minerals. By utilizing the appropriate carrier, the starting bio-stimulant product can be customized to achieve an optimal pH growth environment for the targeted plant.

Once inoculated, zeolite and woodchips have an acidic pH and thus may be the carriers of choice when acidic conditions are optimal for plant health and growth. Water and diatomaceous earth, on the other hand, have a neutral pH. Biochar is alkaline and can be used to buffer acidity in soil, when an alkaline environment is optimal for the targeted plant. When zeolite, biochar, woodchips, or diatomaceous earth is chosen as the carrier, then a further step of drying the carrier may be carried out, so as to remove any access water from the carrier.

During this stage of the process, the carrier is combined with the bio-stimulant at a ratio, for example, of approximately one part bio-stimulant, ten parts carrier and ten parts water by volume. Once the carrier has absorbed and/or adsorbed a sufficient amount of beneficial microorganisms and micronutrients, the carrier may be separated from the aqueous mixture, for example by filtering the carrier containing mixture through a sieve or screen. The recovered carrier is then dried so as to remove excess water and obtain the final bio-stimulant product. The drying process may occur, for example, in the dark (or in the absence of light in the UV spectrum), with dehumidifiers, for a period of time, which may take up to three days for example. Preferably, the drying process occurs in a temperature controlled environment, for example in the range of 15° C. It will be appreciated by a person skilled in the art that other drying procedures may be used and are intended to be included in the present scope of this disclosure. The aqueous mixture that is separated from the carrier may optionally be used as a liquid bio-stimulant product, as a certain amount of micronutrients and/or beneficial microorganisms remain within the aqueous solution.

The pH of the starting bio-stimulant product may be in the range of 3 to 4, as pathogenic microorganisms do not survive in acidic environments.

In some embodiments, the starting bio-stimulant product includes only or consists essentially of microbes or microbial consortia isolated from the natural environment (e.g., from the soil or humus of a thriving plant). In such embodiments, the starting bio-stimulant product does not contain laboratory strains of microorganisms (i.e., microorganisms that are grown in laboratories).

Throughout the foregoing description and the drawings, in which corresponding and like parts are identified by the same reference characters, specific details have been set forth in order to provide a more thorough understanding to persons skilled in the art. However, well known elements may not have been shown or described in detail or at all to avoid unnecessarily obscuring the disclosure.

As will be apparent to those skilled in the art in the light of the foregoing disclosure, many alterations and modifications are possible in the practice of this invention without departing from the scope thereof. Accordingly, the description and drawings are to be regarded in an illustrative, rather than a restrictive, sense.

The invention claimed is:

1. A method of producing a fertilizer composition, comprising the steps of:
   (a) preparing a water in a reactor to reduce a pH of the water to about 2.5 to about 5.5;
   (b) obtaining a starting material from a natural environment, the starting material comprising at least one microorganism;
   (c) preparing a starting bio-stimulant product from the starting material by the steps of:
      (i) preparing a first mixture comprising the starting material, a first carbohydrate and a water;
      (ii) placing the first mixture in a microorganism growth environment for a first time interval so as to cultivate the at least one microorganism;
      (iii) preparing a second mixture by adding a second carbohydrate to the first mixture; and
      (iv) fermenting the second mixture in a first fermentation environment for a second time interval so as to produce the starting bio-stimulant product comprising a plurality of microorganisms,
   (d) adding an organic material, the starting bio-stimulant product, and a starting nitrogen source comprising an inorganic source of nitrogen and/or an organic source of nitrogen, to the water prepared in step (a) to form a fertilizing mixture; and
   (e) increasing a concentration of nitrogen of at least 1.5 times the total combined concentration of nitrogen in the organic material and the starting nitrogen source by fermenting the fertilizing mixture for a third time interval to form a fermented mixture comprising the fertilizer composition.

2. The method as defined in claim 1, further comprising (f) collecting biogas produced from the fermenting of the fertilizing mixture during or after the fermenting of the fertilizing mixture in step (e).

3. The method as defined in claim 1, wherein the inorganic source of nitrogen is one or more salts comprising nitrate ions ($NO_3^-$) and/or ammonium ions ($NH_4^+$).

4. The method as defined in claim 1, wherein the fermenting of the fertilizing mixture in step (e) comprises maintaining an oxygen-limited condition.

5. The method as defined in claim 1, wherein the third time interval is in the range of from about 5 to about 10 days.

6. The method as defined in claim 1, wherein the fermenting of the fertilizing mixture in step (e) comprises maintaining a temperature in the range of from about 20° C. to about 35° C.

7. The method as defined in claim 1, wherein the plurality of microorganisms in the bio-stimulant product comprises facultative anaerobic organisms.

8. The method as defined in claim 1, wherein the organic material comprises an organic waste.

9. The method of claim 8, wherein the organic material is manure.

10. The method as defined in claim 1, further comprising (g) adding a carbon nanomaterial to the prepared water prior to the step of fermenting the fertilizing mixture in step (e).

11. The method as defined in claim 1, wherein the starting nitrogen source is generated from atmospheric air.

12. The method as defined in claim 1, further comprising (h) recycling the liquid fraction for adding to a fresh batch of fertilizing mixture in a subsequent fermentation process.

13. The method as defined in claim 1, wherein the natural environment is soil or humus.

14. The method as defined in claim 1, further comprising the step of (v) adding a carrier to the starting bio-stimulant product after the step of fermenting the second mixture in step (iv).

15. The method according to claim 1, comprising adding one or more fertilizer ingredients to the first mixture prior to fermenting the second mixture in step (iv).

* * * * *